(12) United States Patent
Matsumoto et al.

(10) Patent No.: US 6,774,095 B2
(45) Date of Patent: Aug. 10, 2004

(54) DETERGENT COMPOSITION

(75) Inventors: Chikako Matsumoto, Wakayama (JP); Keiko Hasebe, Wakayama (JP); Takaya Sakai, Wakayama (JP); Makoto Kubo, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/139,348

(22) Filed: May 7, 2002

(65) Prior Publication Data

US 2002/0193266 A1 Dec. 19, 2002

(30) Foreign Application Priority Data

May 24, 2001 (JP) ......................................... 2001-155010

(51) Int. Cl.$^7$ ............................. C11D 1/83; C11D 1/94; C11D 3/26; C11D 3/32
(52) U.S. Cl. ...................... 510/126; 510/127; 510/130; 510/136; 510/137; 510/138; 510/158; 510/159; 510/237; 510/502
(58) Field of Search ............................... 510/127, 126, 510/130, 136, 137, 138, 158, 159, 237, 502

(56) References Cited

U.S. PATENT DOCUMENTS

| | | | | |
|---|---|---|---|---|
| 4,070,309 A | | 1/1978 | Jacobsen | .................... 252/547 |
| 4,595,526 A | * | 6/1986 | Lai | ............................. 252/545 |
| 4,654,163 A | * | 3/1987 | Quack et al. | ................ 252/312 |
| 4,671,894 A | * | 6/1987 | Lamb et al. | ................. 252/545 |
| 5,534,181 A | * | 7/1996 | Henkel et al. | .............. 510/423 |
| 6,187,735 B1 | * | 2/2001 | Gambogi et al. | ........... 510/237 |
| 6,291,419 B1 | * | 9/2001 | D'Ambrogio et al. | ...... 510/425 |
| 6,407,054 B2 | * | 6/2002 | Sakai et al. | ................. 510/501 |

FOREIGN PATENT DOCUMENTS

JP          10-330783          12/1998

OTHER PUBLICATIONS

J. K. Weil, et al., Journal of the American Oil Chemists Society, vol. 48, No. 11, pps. 674–677, "Tallow Alkanolamides: Preparation and Effect on Surfactant Solutions[1]", Nov. 1971.

* cited by examiner

Primary Examiner—Gregory R. Del Cotto
(74) Attorney, Agent, or Firm—Oblon, Spivak, McClelland, Maier & Neustadt, P.C.

(57) ABSTRACT

Disclosed is a detergent composition characterized by low skin irritation, good foamability, easy handling at the time of manufacture, and excellent stability when stored as a product. The detergent composition is a composition which contains a specific amount of (A) a specific amide alcohol and (B) at least one surfactant selected from an anionic surfactant, a nonionic surfactant, and an amphoteric surfactant, wherein the pH (25° C.) of the 20-fold diluted aqueous solution of the composition is 4.5 to 6.8.

15 Claims, No Drawings

DETERGENT COMPOSITION

FIELD OF THE INVENTION

The present invention relates to a detergent composition such as detergent for shampoo, detergent for body wash, detergent for face wash, detergent for hand wash, and detergent for dish wash.

BACKGROUND ART

Heretofore, detergents for shampoo, detergents for body wash, and the like, which were to be washed away after being applied to skin or hair, were mostly composed of detergent bases such as salts of alkyl sulfate, salts of polyoxyalkylene alkyl ether sulfate, etc. However, since the use of such detergent bases alone leads to poor foaming, an amide such as a monoethanolamide or a diethanolamide is also used in order to enhance the foaming property of the detergent.

However, a monoethanolamide is a solid at normal temperature and therefore it presents a handling problem at the time of manufacture. In addition, it presents another problem such as deposition of crystals when stored at a low temperature. On the other hand, a diethanolamide is associated with concern over the possibility of the formation of nitrosamine.

Generally, it is known that the optimum pH values of foaming agents vary depending on the combinations with surfactants.

There is a description that lauroyl N-methylmonoethanolamide is effective as a foam booster for a salt of alkyl sulfate in JAOCS 48(11), 674–677(1971). However, no description is made of skin irritation, pH, and storage stability.

U.S. Pat. No. 4,070,309 describes a composition which has a pH value of 7 to 10 and comprises an anionic surfactant, a nonionic foam booster, and an alkylphenol derivative, wherein myristoyl N-methylmonoethanolamide is an example of the nonionic foam booster. However, this technique cannot improve both of foamability and storage stability at the same time.

Japanese Patent Application Laid-Open (JP-A) No.10-330783 discloses in examples thereof a combination of an amide sulfate ester-based surfactant and coconut oil fatty acid N-methylethanolamide. However, this technique merely discloses effects based on the detergency and foamability of the amide sulfate ester-based surfactant as the main detergent base and the addition of a small amount of coconut oil acid N-methylethanolamide. Accordingly, no mention whatsoever is made of obtaining a detergent composition which causes little skin irritation and ample foaming.

DISCLOSURE OF THE INVENTION

The object of the present invention is to make it possible to produce, with ease in handling, a detergent composition which has low skin irritation, good foamability and excellent stability when stored as a product.

The present inventors found that an amide alcohol having a specific structure exhibits an excellent foamability in a weakly acidic range, which is said to has low skin irritation, and improves stability when stored as a product.

The present invention relates to a detergent composition comprising 0.8 to 20 weight % of (A) an amide alcohol represented by the following general formula (1) [hereinafter referred to as component (A)] and (B) at least one surfactant selected from an anionic surfactant, a nonionic surfactant, and an amphoteric surfactant [hereinafter referred to as component (B)], wherein the pH at 25° C. of the 20-fold diluted aqueous solution of the detergent composition is 4.5 to 6.8.

(1)

In the formula (I), $R^1CO$— is a saturated or unsaturated acyl group which has 6 to 24 carbon atoms and may have a hydroxy group; $R^2$ is a linear or branched alkyl group having 1 to 3 carbon atoms; and R3 is a linear or branched alkylene group having 1 to 6 carbon atoms or alkenylene group having 2 to 6 carbon atoms.

The detergent composition of the present invention can be produced with ease in handling. The detergent composition has good foamability at the time of washing, excellent stability when stored as a product and low skin irritation. Therefore, the detergent composition is most suitable for such uses as detergent for shampoo, detergent for body wash, detergent for face wash, detergent for hand wash, etc.

The composition of the present invention may further contain at least one selected from (C) an antimicrobial agent, (D) a conditioning component, (E) a pearling agent, and (F) a plant extract.

If the composition contains (C) an antimicrobial agent, the composition exhibits a high antimicrobial effect. If the composition contains (D) a conditioning component, the composition provides a comfortable feeling after use and a sufficient conditioning effect to the skin or hair. If the composition contains (E) a pearling agent, the composition provides a good appearance. If the composition contains (F) a plant extract, the composition provides effects, such as a moisturizing effect, an anti-inflammatory effect, and the like, which are characteristic of the extract, while maintaining good stability of the composition.

DETAILED EXPLANATION OF THE INVENTION

In the general formula (1) for the component (A), $R^1CO$— is preferably a saturated or unsaturated acyl group having 8 to 18 carbon atoms. Preferably, the $R^1CO$— groups are acyl groups derived, for example, from octanoic acid, decanoic acid, dodecanoic acid, tetradecanoic acid, hexadecanoic acid, octadecanoic acid, docosanoic acid, linoleic acid, isostearic acid, oleic acid, coconut oil fatty acid, palm oil fatty acid, palm kernel oil fatty acid, etc. Particularly preferably, the $R^1CO$— groups are acyl groups derived from decanoic acid, dodecanoic acid, coconut oil fatty acid, palm oil fatty acid, and palm kernel oil fatty acid, etc. $R^2$ is preferably a methyl group and $R^3$ is preferably an ethylene group.

From the viewpoint of the foamability of the detergent base and the stability when stored as a product, the component (A) is incorporated in a proportion of 0.8 to 20 weight %, preferably 1 to 10 weight %, and more preferably 1 to 5 weight % into the detergent composition of the present invention.

The anionic surfactant, nonionic surfactant, and amphoteric surfactant as the component (B) are selected from those generally used for cosmetics and toiletries, etc.

Examples of the anionic surfactant include salts of alkyl sulfate, salts of polyoxyalkylene alkyl ether sulfate, salts of polyoxyalkylene alkyl ether acetic acid, salts of polyoxyalkylene alkyl ether phosphate, salts of alkyl phosphate, salts of N-acylmethyltaurine, salts of acylglutamic acid, salts of acyloyl-β-alanine, salts of alkylsulfosuccinic acid, salts of polyoxyalkylene alkylsulfosuccinic acid, fatty acid salts, etc. In particular, salts of alkyl sulfate, salts of polyoxyalkylene alkyl ether sulfate, salts of polyoxyalkylene alkyl ether acetic acid, salts of polyoxyalkylene alkyl ether phosphate, and salts of alkyl phosphate are preferable. Further, salts of alkyl sulfate and salts of polyoxyalkylene alkyl ether sulfate are preferable from the viewpoint of higher foamability. These anionic surfactants may be used singly or in a combination of two or more. Particularly preferred an ionic surfactants are those represented by the following general formula (2).

wherein $R^4$ represents a saturated or unsaturated hydrocarbon group having 10 to 18 carbon atoms; n represent a number in the range of 0 to 5; and M represents an alkali metal, an alkaline earth metal, ammonium, an alkanolamine, or a basic amino acid.

In the general formula (2), n is the average of the numbers of moles of ethylene oxide added (hereinafter indicated as EOp) and is preferably 0 to 3 from the viewpoint of foamability. More preferably, n is 1 to 3 because of lower skin irritation. Further, it is preferable that the proportion of the anionic surfactant represented by the general formula (2) is 60 to 100 weight % of the total anionic surfactants.

Examples of the nonionic surfactant include alkyl polyglycosides, polyoxyalkylene (preferably ethylene) alkyl or alkenyl ether, polyoxyalkylenesorbitan fatty acid esters, sorbitan fatty acid esters, polyoxyalkylenesorbitol fatty acid esters, polyoxyalkyleneglycerin fatty acid esters, polyglycerin fatty acid esters, fatty acid monoglycerides, polyethyleneglycol fatty acid esters, fatty acid alkanolamides other than the component (A), etc.

Examples of the amphoteric surfactant include betaine alkylaminoacetates, alkylamine oxides, alkylamide propylbetaine, alkylhydroxysulfobetaines, amidoamino acids (imidazoline-based betaines), etc.

As to the component (B), one or more of the surfactants selected from the anionic surfactant, the nonionic surfactant, and the amphoteric surfactant may be used in combination. From the viewpoint of detergency, the total of the surfactants constituting the component (B) is preferably 5 to 50 weight %, more preferably 10 to 30 weight %, of the detergent composition of the present invention. It is preferable that the component (B) includes an anionic surfactant. In particular, it is preferable that the component (B) includes an anionic surfactant represented by the general formula (2), i.e., a salt of a specific alkyl sulfate or polyoxyalkylene alkyl ether sulfate, from the viewpoint of foamability.

Examples of the antimicrobial agents as the component (C) include triclosan, triclocarban, piroctone olamine, zinc pyrithione, selenium disulfide, 3-methyl-4-(1-methylethyl) phenol, etc. as well as the antimicrobial agents described in "Science of Antiseptics Bactericides for Cosmetics and Medicines" edited by John J Cabara, Fregrance Journals, 1990. Among these antimicrobial agents, triclosan, triclocarban, piroctone olamine, and zinc pyrithione are particularly preferable.

Besides, a cationic surfactant may be used as the component (C). More specifically, the examples include quaternay ammonium salts represented by the following general formula (C1), benzalkonium salts and benzethonium salts represented by the general formula (C2), chlorhexidine salts represented by the general formula (C3), and pyridinium salts represented by the general formula (C4).

wherein $R^5$ and $R^6$ are the same or different and each represents an alkyl group, an alkenyl group, or a hydroxyalkyl group each having 6 to 14 carbon atoms such that the sum of the carbon atoms is 16 to 26; $R^7$ and $R^8$ are the same or different and each represents an alkyl group or a hydroxyalkyl group each having 1 to 3 carbon atoms or a polyoxyethylene group in which the average of the numbers of moles of ethylene oxide added is not more than 10; and Z represents a halogen atom, an anionic residue of an amino acid, a fatty acid, or a phosphoric, phosphonic, sulfonic or sulfuric ester having a straight-chain or branched alkyl or alkenyl group made up of 1 to 30 carbon atoms, or an anionic oligomer or polymer containing a formalin-condensation product of a polycyclic aromatic compound which may have a styrenesulfonic acid whose degree of polymerization is not less than 3 or a hydrocarbon group as a substituent.

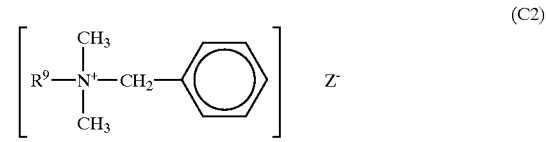

wherein $R^9$ represents a hydrocarbon group having 8 to 14 carbon atoms or the group represented by

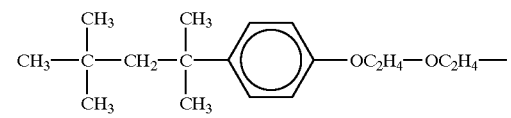

; and Z has the same meaning as above.

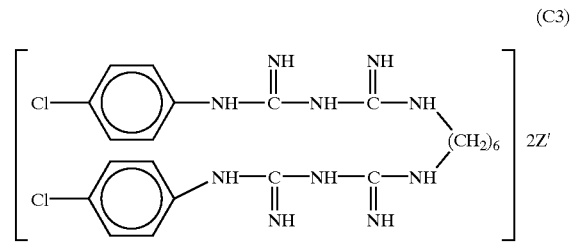

wherein Z' represents gluconic acid, acetic acid, or hydrochloric acid.

wherein $R^{10}$ represents a straight-chain or branched alkyl group having 6 to 18 carbon atoms and Z has the same meaning as above.

In the general formula (Cl), $R^5$ and $R^6$ are preferably an alkyl group having 8 to 12 carbon atoms; and $R^7$ and $R^8$ are preferably an alkyl group having 1 to 3 carbon. In the general formula (C2), $R^9$ is preferably an alkyl group having 8 to 14 carbon atoms. In the general formula (C4), $R^{10}$ is preferably an alkyl group having 8 to 16 carbon atoms. In the general formulae (C1), (C2), and (C4), Z is particularly preferably a halogen atom.

Specific examples of the cationic surfactants that are suitable include benzalkonium chloride, benzethonium chloride, cetylpyridinium chloride, chlorhexidine gluconate, chlorhexidine acetate, chlorhexidine hydrochloride, etc. In particular, the cationic surfactants represented by the general formula (C2), e.g., benzalkonium chloride and benzethonium chloride, are preferable.

A higher effect of the component (C) can be obtained if a combination of a cationic surfactant and an antimicrobial agent other than the cationic surfactant is used.

From the viewpoint of obtaining a sufficient antimicrobial effect, the content of the component (C) in the detergent composition of the present invention is preferably 0.005 to 5 weight %, particularly preferably 0.1 to 4 weight %, and further preferably 0.4 to 3 weight %.

The conditioning component as the component (D) is a component that imparts to the hair and body such properties as smoothness, softness, and moisturizing effect. Specific examples of the conditioning component include oils, silicones, cationic surfactants, and cationic polymers. These may be used singly or in a combination of two or more.

The term "oils" as used herein means solids or liquids which are dispersible in water and ordinarily used in cosmetics and the like and which exclude silicones. Examples of the oils include hydrocarbons such as vaseline; higher fatty acid monoesters such as isopropyl palmitate; higher alcohols such as cetyl alcohol; and plant oils and animal oils such as camellia oil, macadamia nuts oil, mink oil, olive oil, safflower oil, soybean oil, jojoba oil, and lanolin.

One or more kinds of the oils may be used. The content of the oil in the composition is preferably 0.1 to 10 weight %, more preferably 0.2 to 7 weight %, and particularly preferably 0.2 to 5 weight %.

Examples of the silicones include those indicated below.

(1) Dimethylpolysiloxanes represented by the following formula

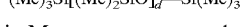

$(Me)_3Si[(Me)_2SiO]_d$—$Si(Me)_3$ wherein Me represents a methyl group and d is a number of 3 to 20000.

(2) Amino-modified silicones

Although various kinds of amino-modified silicones may be used, particularly preferred are those having average molecular weights of about 3000 to 100000 and described under the name of amodimethicone in the CTFA dictionary (U.S.A., Cosmetic Ingredient Dictionary), the third edition. It is preferable that the above-mentioned amino-modified silicones are used as aqueous emulsions. Commercialized products of these amino-modified silicones include SM 8702C (manufactured by Toray Dow Corning Silicone Co. Ltd.) and DC 929 (manufactured by Toray Dow Corning Silicone Co. Ltd.).

(3) Other examples include polyether-modified silicones, methylphenol polysiloxanes, fatty acid-modified silicones, alcohol-modified silicones, alkoxy-modified silicones such as epoxy-modified silicones, fluorine-modified silicones, cyclic silicones, alkyl-modified silicones, etc.

One or more kinds of the silicones may be used. The content of the silicone in the composition is preferably 0.1 to 10 weight %, more preferably 0.2 to 5 weight %, and particularly preferably 0.2 to 3 weight %.

Examples of the cationic surfactant include quaternary ammonium salts represented by the following general formula (3).

wherein at least one of $R^{11}$, $R^{12}$, $R^{13}$, and $R^{14}$ represents an alkyl or alkenyl group which has 16 to 28 carbon atoms and may be substituted with an alkoxy group, alkenyloxy group, alkanoylamino group, or alkenoylamino group each having 16 to 28 carbon atoms so that the rest each represents a benzyl group, an alkyl or hydroxy alkyl group having 1 to 5 carbon atoms, or a polyoxyethylene or polyoxypropylene group in which the sum of the numbers of moles added is not more than 20; and $Z''^-$ represents a halogen ion or an organic anion.

In the general formula (3), it is preferable that one or two of $R^{11}$, $R^{12}$, $R^{13}$, and $R^{14}$ are each a straight-chain or branched alkyl group having 16 to 22 carbon atoms and the rest is a methyl group. Further, it is preferable that $Z''^-$ is a chlorine ion.

Preferred examples of the cationic surfactant include N-stearyl-N,N,N-trimethylammonium chloride, N,N-distearyl-N,N-dimethylammonium chloride, N,N-dibehenyl-N,N-dimethylammonium chloride, etc.

One or more kinds of the cationic surfactants may be used. The content in the composition is preferably 0.01 to 10 weight %, more preferably 0.05 to 10 weight %, and particularly preferably 0.05 to 7 weight %.

Examples of the cationic polymer include cationized cellulose derivatives, cationic starch, cationized guar gum derivatives (e.g., Jaguar C-13'S, Jaguar C-17, and Jaguar C-16 manufactured by Celanese Corporation), homopolymers of diallyl quaternary ammonium salts, diallyl quaternary ammonium salt/acrylamide copolymers, diallyl quaternary ammonium salt/acrylic acid copolymers, diallyl quaternary ammonium salt/acrylic acid/acrylamide ternary copolymers, quaternized polyvinylpyrrolidone derivatives, quaternized vinylpyrrolidone vinylimidazole polymers(e.g., LUVIQUAT manufactured by BASF Corp., etc.), polyglycol/polyamine condensation products, vinylimidazolium trichloride-vinylpyrrolidone copolymers, hydroxyethyl cellulose/dimethyldiallyl chloride copolymers, vinylpyrrolidone/quaternized dimethylamino methacrylate copolymers, polyvinylpyrrolidone/alkylamino acrylate/vinylcaprolactam copolymers, vinylpyrrolidone/methacrylamidopropyl trimethylammonium chloride copolymers, alkyl acrylamide/acrylate/alkylaminoalkyl acrylamide/polyethylene glycol methacrylate copolymers, adipic acid/dimethylaminohydroxypropylethylenetriamine copolymers (e.g., CALTALETINE manufactured by U.S. Sandos Corp., etc.), and cationic polymers described in JP-A NO. 53-139734 and JP-A NO. 60-36407. In particular, cationized cellulose derivatives are preferable.

One or more kinds of the cationic polymers may be used. The content in the composition is preferably 0.01 to 5 weight %, more preferably 0.01 to 3 weight %, and particularly preferably 0.03 to 2 weight %.

One or more kinds of the component (D) may be used. The content in the composition is 0.01 to 20 weight %, preferably 0.1 to 10 weight %, and more preferably 0.1 to 7 weight %.

The pearling agent as the component (E) is a component that can impart a pearl luster to the appearance of the composition. In the present invention, compounds, known as emulsifying agents or pearling agents, such as esters made up of glycols and fatty acids (e.g., monoesters and diesters) and long-chain dialkyl ethers can be used as the pearling agent. Specific examples of the pearling agent include organic compounds such as ethylene glycol distearate, ethylene glycol monostearate, diethylene glycol distearate, ethylene glycol dipalmitate, distearyl ethers, etc. From the viewpoint of costs and availability, esters made up of glycols and fatty acids are suitable. In particular, ethylene glycol monostearate and ethylene glycol distearate are suitable. More particularly, ethylene glycol distearate is preferable.

The content of the component (E) in the composition is preferably not less than 0.3 weight % and less than 10 weight %, more preferably 1.0 to 5.0 weight %, and most preferably 1.0 to 4.0 weight % from the viewpoint of appearance.

The appearance of the detergent composition of the present invention has a pearl luster. This composition can be prepared, for example, by the steps of melting a mixture of the component (A), the component (B), the component (E), and water with stirring by heating up to a temperature not less than the melting point of the component (E) so as to produce a homogeneous state, adding optional components to the homogeneous mixture, and cooling the mixture while being stirred so that the crystals of the component (E) are deposited. Alternatively, it is possible to prepare the composition by the steps of melting a mixture of the component (B), the component (C), and water with stirring by heating up to a temperature not less than the melting point of the component (E), adding the component (E) and dissolving homogeneously the component (E), adding optional components, and cooling the mixture while being stirred so that the crystals of the component (E) are deposited.

Further, it is possible to prepare the detergent composition by the steps of preparing a concentrated pearling composition in advance and incorporating the concentrated composition into the detergent composition at the time of manufacture thereof at a temperature not more than the melting point of the component (E).

The concentrated pearling composition is a composition having an appearance of pearl luster. Examples of the composition include EUPERLAN series of COGNIS Corp. A preferred example is the following composition.

A composition containing:
the pearling agent as the component (E) in an amount of 10 to 50 weight %, preferably 15 to 30 weight %;
the component (B) in an amount of 10 to 50 weight %, preferably 10 to 35 weight %; and
the component (A) in an amount of 0.1 to 20 weight %, preferably 0.5 to 15 weight %.

The detergent composition of the present invention, which is obtained in the above-described way, exhibits good dispersion stability of the component (E) in the product. Therefore, the detergent composition of the present invention is most suitable as a detergent composition having a pearl luster and examples of the composition include detergents for shampoo, detergents for body wash, detergents for face wash, detergents for hand wash, etc.

Examples of the plant extract as the component (F) include the plant-based extracted essences commercialized by ICHIMARU FALCOS Co., Ltd. Specific examples thereof include aloe, aloe vera, ginkgo, fennel, seaweeds, root of kudzu, chamomile, kiwi, cucumber, luffa, gardenia, rice bran, peach, yuzu, adlay, etc.

The content of the plant extract as the component (F) in the composition is preferably 0.001 to 10 weight %, more preferably 0.005 to 5.0 weight %, and most preferably 0.01 to 3 weight % from the viewpoint of stability and moisturizing effect.

The pH (25° C.) of the 20-fold diluted aqueous solution of the detergent composition of the present invention is 4.5 to 6.8, preferably 5.5 to 6.8, because these pH values fall in the closeness of the pH of healthy human skin.

The detergent composition of the present invention can be prepared with ease in handling at the time of manufacture and the detergent composition has a good foamability when used, has excellent stability when stored as a product, and has a low skin irritation. Therefore, the detergent composition is most suitable as a detergent for shampoo, a detergent for body wash, a detergent for face wash, a detergent for hand wash, etc.

Further, the composition provides a high antimicrobial effect if the composition is incorporated with an antimicrobial agent; the composition provides a good feeling after use or a sufficient conditioning effect to the skin or hair if the composition is incorporated with a conditioning component; and the composition provides a good appearance if the composition is incorporated with a pearling agent.

The detergent composition of the present invention may appropriately contain water-soluble polymers such as methyl cellulose, hydroxyethyl cellulose, carboxyvinyl polymers, and poly saccharides (xanthan gums); solubilizers such as glycerin, sorbitol, and ethanol; chelating agents such as ethylenediaminetetraacetic acid (EDTA), and phosphonates; antiseptics such as parabens and benzoic acid; anti-inflammatory agents such as dipotassium glycyrrhizinate and allantoin; antioxidants such as dibutylhydroxytoluene; ultraviolet absorbers; pH adjusting agents such as malic acid, citric acid, potassium hydroxide, and sodium hydroxide; dyes; perfumes; etc.

Further, the detergent composition of the present invention may take any of such forms as solid, liquid, paste, etc.

EXAMPLES

| | (parts by weight) |
|---|---|
| Example 1 Shampoo | |
| Sodium polyoxyethylene (EOp = 2) lauryl ether sulfate | 15.0 |
| Alkyl polyglucoside [MYDOL 10 (content of effective component: 40 weight %) manufactured by Kao Corporation] | 4.0 |
| N-ethanol-N-methyl dodecanoic acid amide | 3.0 |
| EDTA.2Na | 0.3 |
| pH adjusting agent* (malic acid) | q.s. |
| Preservative | 0.5 |
| Purified water | balance |
| Total | 100.0 |

*pH adjusting agent: used in such an amount that caused pH (25° C.) of the 5 weight % aqueous solution (20-fold diluted aqueous solution) of the shampoo to become 6.0.

| Example 2 Detergent for body wash | |
|---|---|
| Sodium polyoxyethylene (EOp = 2) lauryl ether sulfate | 16.0 |
| Sodium polyoxyethylene (EOp = 4.5) alkyl (number of carbon atoms: 12, 14) ether acetate | 5.0 |
| N-ethanol-N-methyl palm kernel oil fatty acid amide | 2.5 |
| Glycerin | 3.0 |
| Cationized cellulose [POIZ C-80M manufactured by Kao corporation] | 0.1 |
| Ethylene glycol distearate | 3.0 |
| EDTA.2Na | 0.3 |

-continued

| | (parts by weight) |
|---|---|
| pH adjusting agent* (citric acid) | q.s. |
| Preservative | 0.5 |
| Purified water | balance |
| Total | 100.0 |

*pH adjusting agent: used in such an amount that caused pH (25° C.) of the 5 weight % aqueous solution (20-fold diluted aqueous solution) of the detergent for body wash to become 5.7.

Example 3 Detergent for face wash

| | (parts by weight) |
|---|---|
| Sodium polyoxyethylene (EOp = 2) lauryl ether sulfate | 20.0 |
| N-ethanol-N-methyl dodecanoic acid amide | 4.8 |
| Glycerin | 3.0 |
| Hydroxyethyl cellulose [HEC-850SE manufactured by Daicel Ltd.] | 0.3 |
| Ethylene glycol distearate | 1.5 |
| EDTA.2Na | 0.3 |
| pH adjusting agent* (citric acid) | q.s. |
| Preservative | 0.5 |
| Purified water | balance |
| Total | 100.0 |

*pH adjusting agent: used in such an amount that caused pH (25° C.) of the 5 weight % aqueous solution (20-fold diluted aqueous solution) of the detergent for face wash to become 6.0.

Example 4 Shampoo

| | (parts by weight) |
|---|---|
| Sodium polyoxyethylene (EOp = 2) lauryl ether sulfate | 16.0 |
| N-ethanol-N-methyl dodecanoic acid amide | 3.0 |
| Cationized cellulose [POIZ C-60H manufactured by Kao Corporation] | 0.3 |
| Zinc pyrithione | 0.5 |
| Benzalkonium chloride | 0.5 |
| Ethylene glycol distearate | 3.0 |
| EDTA.2Na | 0.3 |
| pH adjusting agent* | q.s. |
| Preservative | 0.5 |
| Purified water | balance |
| Total | 100.0 |

*pH adjusting agent: used in such an amount that caused pH (25° C.) of the 5 weight % aqueous solution (20-fold diluted aqueous solution) of the shampoo to become 6.0.

Example 5

Preparation of a Pearling Agent Concentrate

A perling agent concentrate was prepared by the steps of heating a mixture of 5 parts by weight of N-ethanol-N-methyl coconut oil fatty acid amide as the component (A), 10 parts by weight of polyoxyethylene (EOp=4) lauryl ether and 3 parts by weight of lauramidopropyl betaine as the component (B), 15 parts by weight of ethylene glycol distearate and 5 parts by weight of ethylene glycol monostearate as the component (E), and 62 parts by weight of water to 70 to 75° C., thereafter cooling the mixture with stirring so as to crystalize the component (E), and further cooling the mixture with stirring to room temperature.

Shampoo

| | (parts by weight) |
|---|---|
| Sodium polyoxyethylene (EOp = 2) lauryl ether sulfate | 15.0 |
| N-ethanol-N-methyl coconut oil fatty acid amide | 3.3 |
| Sodium polyoxyethylene (EOp = 4.5) lauryl ether acetate | 3.8 |
| Cationized cellulose [POIZ C-80M manufactured by Kao Corporation] | 0.4 |
| Pearling agent concentrate | 10.0 |
| EDTA.2Na | 0.3 |
| pH adjusting agent* | q.s. |
| Preservative | 0.5 |
| Purified water | balance |
| Total | 100.0 |

*pH adjusting agent: used in such an amount that caused pH (25° C.) of the 5 weight % aqueous solution (20-fold diluted aqueous solution) of the shampoo to become 6.2.

The detergent composition s of Examples 1 to 5 were all prepared in an ordinary way. All of the detergent composition s obtained exhibited good foamability and low skin irritation when used. The storage stability was also excellent.

Besides, the composition of Example 4, which contained an antimicrobial agent, had a high antimicrobial effect; and the composition of Example 2, which contained a conditioning component, gave a good feeling after use on the skin. The composition of Example 5, which contained a pearling agent, had a good appearance.

Example 6 Hand soap

| | (parts by weight) |
|---|---|
| Sodium polyoxyethylene (EOp = 2) lauryl ether sulfate | 13.0 |
| N-ethanol-N-methyl coconut oil fatty acid amide | 3.0 |
| Cocamidopropyl betaine | 1.0 |
| Ethylene glycol distearate | 2.5 |
| EDTA.2Na | 0.2 |
| Seaweed extract | 0.1 |
| pH adjusting agent* | q.s. |
| Preservative | 0.3 |
| Purified water | balance |
| Total | 100.0 |

*pH adjusting agent: used in such an amount that caused pH (25° C.) of the 5 weight % aqueous solution (20-fold diluted aqueous solution) of the shampoo to become 6.0.

Example 7

The detergent composition s listed Table 1 were prepared according to a ordinary method. The foamability, storage stability, skin irritation, inhibition of dandruff formation, deodorant effect, and conditioning effect were assessed.

(1) Foamability (Foaming)

Five men and five women as panelists each washed the body with each of the detergent composition s listed in Table 1 and sensory evaluation of the foamability was made according to the following criteria.

5: they had a feeling that the foamability was good
4: they had a feeling that the foamability was fairly good
3: they had a feeling that the foamability was ordinary
2: they had a feeling that the foamability was poor
1: they had a feeling that the foamability was bad.

The averages of the figures given by the 10 panelists were expressed as foamability based on the following criteria.
◎: average was not less than 4.0 (good)
○: average was 3.2 to 3.9 (fairly good)
Δ: average was 2.5 to 3.1 (ordinary)
X: average was not more than 2.4 (bad).

(2) Storage Stability

The detergent composition s listed in Table 1 were stored at 0° C. and the appearance of the compositions after the storage was compared with the appearance of the compositions immediately after preparation thereof. Evaluations were made according to the following criteria.
○: appearance did not change for not less than 20 days in comparison with the appearance immediately after preparation
Δ: appearance changed after a period of 7 to 19 days in comparison with the appearance immediately after preparation
X: appearance changed after a period of 0 to 6 days in comparison with the appearance immediately after preparation.

(3) Skin Irritation (Irritation of the Skin) Irritation:

5-fold diluted aqueous solutions of the detergent composition s were prepared. 10 mL of each of the aqueous solutions was placed in a glass cup having a diameter of 3.5 cm held on the forearm of each of the 15 expert panelists and thus the aqueous solution was brought into a direct contact with the skin for 30 minutes per day. After this procedure was carried out for 3 consecutive days, the skin condition was evaluated according to the following criteria.
○: desquamation was observed for not more than 8 persons
Δ: desquamation was observed for not less than 9 persons but no erythema was observed
X: desquamation and erythema were observed for not less than 9 persons.

(4) Inhibition of Dandruff

Seven male panelists were selected and their shampoo was stopped for 48 hours. After that, each of them washed the hair twice using 3 g of the following detergent composition (A) for each wash and the total washing liquid was recovered.

* Detergent composition (A)

|  | (parts by weight) |
|---|---|
| Sodium polyoxyethylene (EOp = 2) lauryl ether sulfate | 15.0 |
| Cocamidopropyl betaine | 3.0 |
| pH adjusting agent (in such an amount that caused pH at 25° C. to become 6.0) | q.s. |
| Ion-exchanged water | balance |
| Total | 100.0 |

The total washing liquid recovered was filtered through a 50-meshnylon sieve so as to remove unnecessary dirts and hair. Next, the total filtrate was filtered through a 255-mesh nylon sieve (100 μm×100 μm) whose weight had been measured in advance. The 255-mesh nylon sieve was then dried for 48 hours at room temperature and the weight of the keratin captured by the 255-mesh nylon sieve was taken as the dandruff initial weight.

After that, the detergent composition s listed in Table 1 were each allotted to every person, who washed the hair using each detergent composition once per day. When one month passed, they stopped shampooing for 48 hours. Again, each of them washed the hair twice using 3 g of the detergent composition for each wash and the total washing liquid was recovered. In the same way as above, the keratin weight was measured and the value obtained was taken as the dandruff weight on test.

Based on the dandruff initial weight and the dandruff weight on test, (the dandruff initial weight/the dandruff weight on test) X100 was obtained. If the value thus obtained was more than 95, the dandruff inhibition rated as X; if the value thus obtained was more than 75 and not more than 95, the dandruff inhibition rated as Δ; if the value thus obtained was more than 60 and not more than 75, the dandruff inhibition rated as ○; and if the value thus obtained was not more than 60, the dandruff inhibition rated as ◎.

(5) Deodorant Effect

Five male panelists and five female panelists each washed head using one of the detergent composition s once per day for 2 weeks. After the final wash, when 48 hours passed, expert appraisers tested the odor of the head and evaluation was made according to the following criteria.

5: no odor was scented
4: odor was scented faintly
3: odor was scented
2: odor was scented significantly
1: fairly strong odor was scented.

The averages of the figures given by the 10 panelists were expressed as deodorant effect according to the following criteria.
◎: average was not less than 4.0 (good)
○: average was 3.2 to 3.9 (fairly good)
Δ: average was 2.5 to 3.1 (ordinary)
X: average was not more than 2.4 (bad).

(6) Conditioning Effect

Five male panelists and five female panelists each washed tress using one of the detergent composition s listed in Table 1. At the time of washing, the sensory evaluation of conditioning effect was made according to the following criteria.

4: they had a feeling that the conditioning effect was good
3: they had a feeling that the conditioning effect was fairly good
2: they had a feeling that the conditioning effect was not so good
1: they had a feeling that the conditioning effect was poor.

The averages of the figures given by the 10 panelists were expressed as conditioning effect according to the following criteria.
○: average was not less than 3.5 (good)
Δ: average was more than 2.5 and less than 3.5 (fairly good)
X: average was not more than 2.5 (poor).

TABLE 1

|  |  |  | \multicolumn{8}{c|}{Samples of the present invention} | \multicolumn{2}{c}{Comparative Samples} |
|---|---|---|---|---|---|---|---|---|---|---|---|---|
|  |  |  | 1 | 2 | 3 | 4 | 5 | 6 | 7 | 8 | 1 | 2 |
| Composition (weight %) | Component (A) | N-ethanol-N-methyl palm kernel oil fatty acid amide | 2.0 |  | 1.5 |  | 2.0 | 3.0 | 2.4 |  |  |  |
|  |  | N-ethanol-N-methyl dodecanoic acid amide |  | 2.5 |  | 3.0 |  |  |  | 3.7 |  |  |
|  | Component (B) | Sodium polyoxyethylene (EOp = 2) lauryl ether sulfate | 18.0 | 15.0 | 16.0 | 10.0 | 9.0 | 15.0 | 17.0 | 15.0 | 15.0 | 15.0 |
|  |  | Sodium polyoxyethylene (EOp = 4.5) lauryl ether acetate |  |  |  |  | 9.0 |  |  |  |  |  |
|  |  | Cocamidepropyl betaine |  |  |  | 2.0 | 1.0 |  |  |  |  |  |
|  |  | Alkyl polyglucoside[1] |  | 5.0 |  |  | 10.0 |  |  |  |  |  |
|  |  | Sodium lauryl sulfate |  |  |  |  |  | 2.0 |  |  |  |  |
|  | Component (C) | Piroctone elamine |  |  |  |  |  | 1.0 |  |  |  |  |
|  |  | Benzalkonium chloride (number of carbon atoms in alkyl group: 12) |  |  |  |  |  | 0.2 |  |  |  |  |
|  | Component (D) | Amino-modified silicone(1)[2] |  |  |  |  |  |  |  | 0.5 |  |  |
|  |  | Cationized cellulose derivative(1)[3] |  |  |  |  |  |  | 0.4 |  |  |  |
|  |  | Cationic surfactant(1)[4] |  |  |  |  |  |  | 2.0 |  |  |  |
|  |  | Lauroyl monoethanolamide |  |  |  |  |  |  |  |  |  | 3.5 |
|  |  | pH adjusting agent* (malic acid) | q.s. | q.s. | q.s. | q.s. | q.s. | q.s. | q.s. | q.s. | q.s. | q.s. |
|  |  | Ion-exchanged water | Balance | Balance | Balance | Balance | Balance | Balance | Balance | Balance | Balance | Balance |
|  |  | Total | 100 | 100 | 100 | 100 | 100 | 100 | 100 | 100 | 100 | 100 |
|  | pH (25° C.) of the 20-fold diluted aqueous solution |  | 6.0 | 6.2 | 6.3 | 6.5 | 6.0 | 6.6 | 6.2 | 6.2 | 10.0 | 6.5 |
|  |  | Foamability | ⊚ | ⊚ | ⊚ | ⊚ | ○ | ⊚ | ⊚ | ⊚ | X | ○ |
|  |  | Storage stability | ○ | ○ | ○ | ○ | ○ | ○ | ○ | ○ | ○ | X |
|  |  | Skin irritation | ○ | ○ | ○ | ○ | ○ | ○ | ○ | ○ | Δ | ○ |

*The pH adjusting agents were each used in such an amount that caused pH (25° C.) of the 20-fold diluted aqueous solutions to become the figures shown in the table.
Note
[1]Alkyl polyglucoside: number of carbon atoms in alkyl group : 9~11, condensation degree: 1~1.35
[2]Amino-modified silicone (1): SM 8702C manufactured by Toray Dow Corning Silicone Co. Ltd.
[3]Cationized cellulose derivative (1): POIZ C-80M manufactured by Kao Corporation
[4]Cationic surfactant (1) :N,N-distearyl-N,N-dimethylammonium chloride
Results of evaluations of dandruff inhibition, deodorant effect, and conditioning effect:
Composition 6 of the present invention gave dandruff inhibition ⊚ and deodorant effect ⊚.
Composition 7 of the present invention gave conditioning effect ○.
Composition 8 of the present invention gave conditioning effect ○.

What is claimed is:

1. A detergent composition, comprising:
0.8 to 20 weight % of (A) an amide alcohol represented by the following formula (1) and
(B) at least one surfactant selected from the group consisting of an anionic surfactant, a nonionic surfactant and an amphoteric surfactant;
wherein the pH at 25° C. of the 20-fold diluted aqueous solution of said detergent composition is from 4.5 to 6.8,

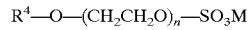

(1)

wherein the formula (1), $R^1CO-$ is a saturated or unsaturated acyl group which has 6 to 24 carbon atoms and may have a hydroxy group; $R^2$ is a linear or branched alkyl group having 1 to 3 carbon atoms; and $R^3$ is a linear or branched alkylene group having 1 to 6 carbon atoms or alkenylene group having 2 to 6 carbon atoms.

2. The detergent composition according to claim 1, wherein the surfactant (B) is at least one anionic surfactant.

3. The detergent composition according to claim 1 or 2, wherein the surfactant (B) is an anionic surfactant represented by the following general formula (2);

$$R^4-O-(CH_2CH_2O)_n-SO_3M$$

wherein $R^4$ represents a saturated or unsaturated hydrocarbon group having 10 to 18 carbon atoms; n represents a number in the range of 0 to 5; and M represents an alkali metal, an alkaline earth metal, ammonium, an alkanolamine or a basic amino acid.

4. The detergent composition according to claim 3, wherein the proportion of the anionic surfactant represented by the general formula (2) accounts for 60 to 100 weight % of the total anionic surfactants.

5. The detergent composition according to claim 1, which further comprises at least one member selected from the group consisting of (C) an antimicrobial agent, (D) a conditioning component, (E) a pearling agent, and (F) a plant extract.

6. The detergent composition according to claim 2, which further comprises at least one member selected from the group consisting of (C) an antimicrobial agent, (D) a conditioning component, (E) a pearling agent, and (F) a plant extract.

7. The detergent composition according to claim 3, which further comprises at least one member selected from the group consisting of (C) an antimicrobial agent, (D) a conditioning component, (E) a pearling agent, and (F) a plant extract.

8. The detergent composition according to claim 4, which further comprises at least one member selected from the group consisting of (C) an antimicrobial agent, (D) a conditioning component, (E) a pearling agent, and (F) a plant extract.

9. The detergent composition according to claim 1, wherein the surfactant (B) is at least one anionic surfactant selected from the group consisting of a salt of an alkylsulfate, a salt of a polyoxyalkylene alkyl ether sulfate, a salt of a polyoxyalkylene alkyl ether acetic acid, a salt of a polyoxyalkylene alkyl ether phosphate, a salt of an alkylphosphate, a salt of an N-acylmethyltaurine, a salt of an acylgiutamic acid, a salt of an acyloxyl-β-alanine, a salt of an alkylsulfosuccinic acid, a salt of a polyoxyalkylene alkylsulfosuccinic acid, and a fatty acid salt.

10. The detergent composition according to claim 1, wherein the amide alcohol (A) represented by formula (1) is present in an amount that ranges from 1 to 10 wt. %.

11. The detergent composition according to claim 1, wherein the amide alcohol (A) represented by formula (1) is present in an amount that ranges from 1 to 5 wt. %.

12. The detergent composition according to claim 5, wherein the plant extract is at least one selected from the group consisting of aloe, aloe vera, ginkgo, fennel, seaweeds, root of kudzu, chamomile, kiwi, cucumber, luffa, gardenia, rice bran, peach, yuzu, and adlay.

13. The detergent composition according to claim 6, wherein the plant extract is at least one selected from the group consisting of aloe, aloe vera, ginkgo, fennel, seaweeds, root of kudzu, chamomile, kiwi, cucumber, luffa, gardenia, rice bran, peach, yuzu, and adlay.

14. The detergent composition according to claim 7, wherein the plant extract is at least one selected from the group consisting of aloe, aloe vera, ginkgo, fennel, seaweeds, root of kudzu, chamomile, kiwi, cucumber, luffa, gardenia, rice bran, peach, yuzu, and adlay.

15. The detergent composition according to claim 8, wherein the plant extract is at least one selected from the group consisting of aloe, aloe vera, ginkgo, fennel, seaweeds, root of kudzu, chamomile, kiwi, cucumber, luffa, gardenia, rice bran, peach, yuzu, and adlay.

* * * * *